United States Patent
Hansen et al.

(10) Patent No.: US 11,324,612 B2
(45) Date of Patent: May 10, 2022

(54) BREATHABLE RESIDUAL-LIMB SOCKET SYSTEM

(71) Applicant: The United States Government as represented by the Department of Veterans Affairs, Washington, DC (US)

(72) Inventors: Andrew H. Hansen, Apple Valley, MN (US); Eric A. Nickel, Brooklyn Park, MN (US); Billie Caris Savvas Slater, Mendota Heights, MN (US); Stuart R. Fairhurst, Minneapolis, MN (US); Jennifer Leestma, Wayzata, MN (US)

(73) Assignee: United States Government as Represented by the Department of Veterans Affairs, Washington, DC (US)

( * ) Notice: Subject to any disclaimer, the term of this patent is extended or adjusted under 35 U.S.C. 154(b) by 61 days.

(21) Appl. No.: 17/025,008

(22) Filed: Sep. 18, 2020

(65) Prior Publication Data

US 2021/0085493 A1 Mar. 25, 2021

Related U.S. Application Data

(60) Provisional application No. 62/903,289, filed on Sep. 20, 2019.

(51) Int. Cl.
*A61F 2/78* (2006.01)
*A61F 2/80* (2006.01)
*A61F 2/60* (2006.01)

(52) U.S. Cl.
CPC .............. *A61F 2/7812* (2013.01); *A61F 2/78* (2013.01); *A61F 2/80* (2013.01); *A61F 2/60* (2013.01);
(Continued)

(58) Field of Classification Search
CPC .. A61F 2/78; A61F 2/7812; A61F 2/80; A61F 2002/7837; A61F 2002/7893;
(Continued)

(56) References Cited

U.S. PATENT DOCUMENTS 9,925,072 B2 * 3/2018 Jonsson .................... A61F 2/80
2019/0374355 A1 * 12/2019 Storup ..................... A61F 7/10
(Continued)

FOREIGN PATENT DOCUMENTS

EP 0182412 A1 * 5/1986 ........... A61F 2/7812

*Primary Examiner* — Bruce E Snow
(74) *Attorney, Agent, or Firm* — Ballard Spahr LLP

(57) ABSTRACT

A liner defines a pouch, an opening, a cup, and a first ring positioned on the pouch distal to the opening. The pouch is air-permeable and defines an internal volume for receiving a residual limb. The opening defined by the pouch provides access to the internal volume. The cup is air-impermeable and is positioned on the pouch distal to the opening. The liner is combined with an adapter for connecting a residual limb to a prosthetic limb. The adapter has a socket for receiving the cup, at least one hole positioned within the socket for drainage therefrom and sleeve extending from the socket and surrounding a central space. The adapter also has at least one vent positioned in the sleeve and overlies the air permeable material.

18 Claims, 8 Drawing Sheets

(52) U.S. Cl.
CPC ............. *A61F 2002/7837* (2013.01); *A61F 2002/7893* (2013.01); *A61F 2002/802* (2013.01); *A61F 2002/805* (2013.01); *A61F 2002/807* (2013.01)

(58) Field of Classification Search
CPC .......... A61F 2002/802; A61F 2002/805; A61F 2002/807
See application file for complete search history.

(56) References Cited

U.S. PATENT DOCUMENTS

| | | | | |
|---|---|---|---|---|
| 2021/0085493 A1* | 3/2021 | Hansen | ................ | A61F 2/7812 |
| 2021/0137707 A1* | 5/2021 | Hansen | ................ | A61F 2/5044 |
| 2021/0401595 A1* | 12/2021 | Kurth | ................... | A61F 2/7812 |

* cited by examiner

BREATHABLE RESIDUAL-LIMB SOCKET SYSTEM

CROSS REFERENCE TO RELATED APPLICATION

This application is based upon and claims benefit of priority to U.S. Provisional Application No. 62/903,289, filed Sep. 20, 2019, which application is hereby incorporated by reference herein.

STATEMENT REGARDING FEDERALLY SPONSORED RESEARCH

This invention was made with government support under Contract No. W81XWH-14-2-0197, awarded by the Department of Defense. The government may have certain rights in the invention.

FIELD OF THE INVENTION

This invention concerns a liner adapted to receive a residual limb, and an adapter for connecting the liner to a prosthesis (prosthetic limb).

BACKGROUND

Prostheses, particularly lower limb prostheses, include liners for receiving the residual limbs and adapters, also referred to as sockets, for connecting the liners to the prostheses. Active individuals using these prostheses commonly complain about discomfort resulting from heat and perspiration. Excess perspiration can result in fluid accumulation within the liner and loss of suspension between the liner and the adapter that occurs when the limb becomes overly moist from perspiration. The loss of suspension results in relative movement between the liner and the adapter, referred to as a "pistoning" motion that can cause blisters and sores as well as discomfort. Heat and perspiration result in two problems. First, interrupting activity, when the prosthesis is removed to dry the limb. Second, a breakdown of skin, if the moisture problem is ignored and relative movement between the liner and the adapter continues.

Sockets designed to remove perspiration by means of miniature pumps and solenoid airflow control systems have been developed. These systems, while effective in expelling moisture, require an active pumping mechanism that adds weight, requires batteries and electronics and increases the inconvenience for the user. Other socket systems were design with a helical cooling channel incorporated within the socket wall. This approach requires carrying a chamber of liquid coolant and a pumping mechanism to circulate the fluid in the socket. Liners received by the sockets, have been developed with small pores allowing moisture to permeate through the liner. These systems allow moisture to migrate from the skin into the space between the liner and the socket. However, the pores in these liners are so small that air cannot penetrate inward to the skin for evaporative cooling.

There is clearly a need to develop liner and socket systems with air permeable liners and socket combinations that remove excess moisture while maintaining suspension between the prosthesis and the liner.

SUMMARY

This invention concerns a liner adapted to receive a residual limb. The liner comprises a pouch, an opening, a cup, and a first ring seal. The pouch defines an internal volume for receiving the limb. The opening defined by the pouch provides access to the internal volume. The cup is positioned on the pouch distal to the opening. The cup is air impermeable. The first ring seal is attached to the pouch and surrounds the cup.

By way of example, the liner further comprises a second ring seal surrounding the cup. The second ring seal is in spaced apart relation to the first ring seal. In a particular example, the second ring seal is oriented parallel to the first ring seal.

In an example, the pouch comprises an air permeable material. By way of example, the liner further comprises a plurality of apertures positioned in the cup.

In another example, the second seal ring seal is positioned farther from the opening than the first ring seal. In a particular example, the liner further comprises a plurality of apertures positioned in the cup. The apertures are surrounded by the second ring seal.

By way of example, the liner further comprises a seam defining a split in the pouch. The split extends from the opening. In a particular example, the liner further comprises a closure positioned along the seam. As an example the closure comprises a zipper.

This invention also concerns an adapter for connecting a residual limb to a prosthetic limb. The adapter comprises a socket for receiving the residual limb, at least one hole, and a sleeve. The at least one hole is positioned within the socket for drainage therefrom. The sleeve extends from the socket and surrounds a central space. As an example the adapter further comprises at least one vent positioned in the sleeve.

This invention further concerns in combination, a liner and an adapter. The liner is adapted to receive a residual limb and the adapter is adapted for connecting the liner to a prosthetic. The liner comprises a pouch, an opening, a cup, and a first ring seal. The pouch defines an internal volume for receiving the limb. The opening is defined by the pouch and provides access to the internal volume. The cup is positioned on the pouch distal to the opening. The cup is air-impermeable. The first ring seal is attached to the pouch and surrounds the cup. The adapter comprises a socket for receiving the cup, at least one hole, and a sleeve. The socket engages the first ring seal. The at least one hole is positioned within the socket for drainage therefrom. The sleeve extends from the socket and surrounds a central space.

As an example, the adapter further comprises at least one vent positioned in the sleeve. In a particular example, the pouch comprises an air-permeable material. By way of example, the at least one vent overlies the air-permeable material.

By way of example, the combination further comprises an interface to the prosthetic. The interface in this example is attached to a posterior surface of the sleeve. In an example, the combination further comprises another interface to the prosthetic. In this example, the interface is attached to a distal end of the adapter.

As an example, the combination further comprises a plurality of apertures positioned in the cup. The apertures face the at least one hole. In a particular example, the combination further comprises an interface to the prosthetic. The interface is attached to a posterior surface of the sleeve. In another particular example, the combination further comprises an interface to the prosthetic. In this example, the interface is attached to a distal end of the adapter.

By way of example, the combination further comprises a second ring seal surrounding the cup. The second ring seal being in spaced apart relation to the first ring seal. The socket engages the second ring seal. In a particular example, the second ring seal is oriented parallel to the first ring seal. In a particular example, the second ring seal is positioned farther from the opening than the first ring seal.

As an example, the combination further comprises a plurality of apertures positioned in said cup. The apertures are surrounded by the second ring seal. The apertures face the at least one hole.

DETAILED DESCRIPTION

Figure 1:
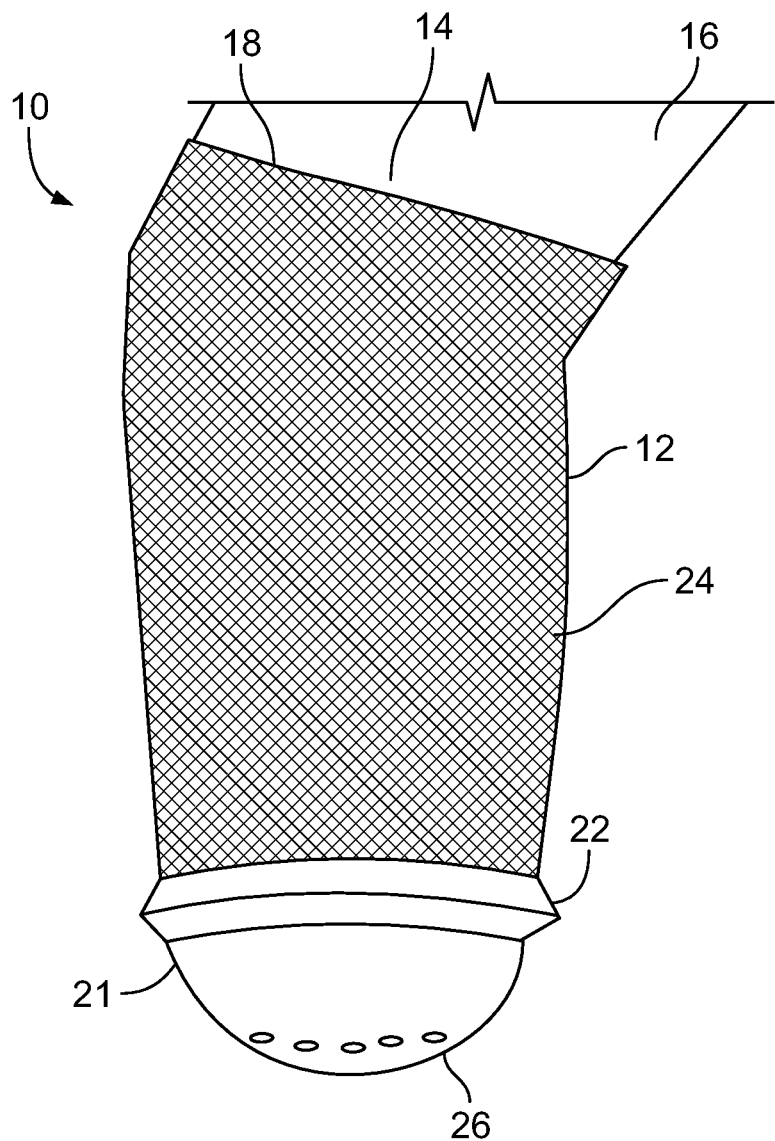
FIG. 1 is a side view of an example embodiment of a liner according to the invention.

FIG. 1 shows an example embodiment of a liner 10 according to the invention. Liner 10 comprises a pouch 12 defining an internal volume 14 for receiving a residual limb 16. Access to the internal volume 14 is provided by an opening 18 defined by the pouch 12. A cup 21 is positioned on the pouch 12 distal to the opening 18. Because the cup 21 bears against the residual limb when in use, the cup may preferably be sufficiently thick to provide cushioning and comfort. The cup 21 is air and liquid impermeable. A first ring seal 22 is attached to the pouch 12 and surrounds the cup 21.

The pouch 12 comprises an air-permeable material 24 to facilitate passive evaporative cooling of the residual limb. The pouch may be fabricated from a soft silicone or polyurethane material incorporating a large surface area of perforations. The pouch 12 further comprises a plurality of apertures 26 positioned in the cup 21. The apertures 26 provide a fluid path away from the residual limb.

Figure 2:
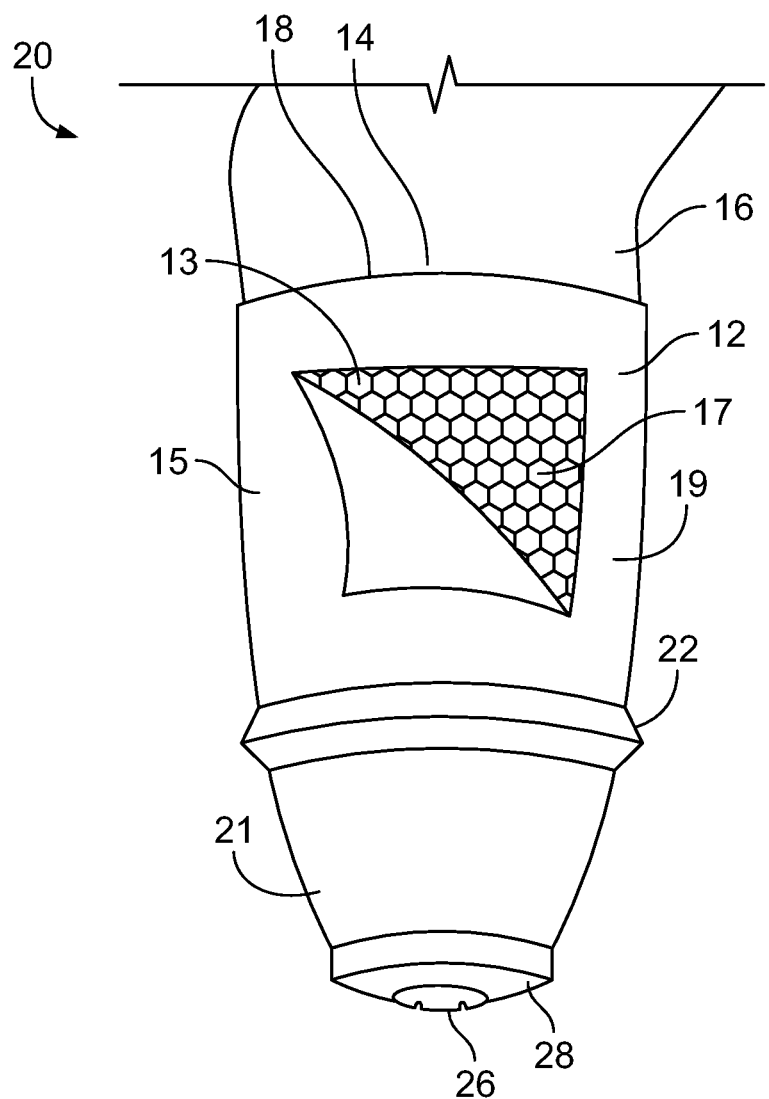
FIG. 2 is a side view of an example embodiment of a liner according to the invention.
Figure 2A:
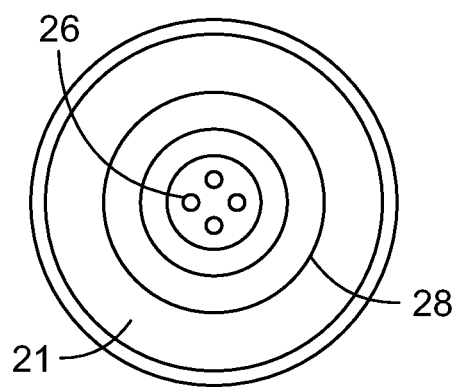
FIG. 2A is a bottom view of an example embodiment of the liner shown in FIG. 2.

FIG. 2 shows an additional example embodiment of liner 20. The pouch 12 comprises an inner surface 13 and an outer surface 15. The inner surface 13 includes a breathable cushion region 17 and the outer surface 15 includes a highly breathable fabric 19. In this embodiment a second ring seal 28 surrounds the cup 21 and is in spaced apart relation to the first ring seal 22. The addition of the second ring seal 28 provides additional contact points to improve suction and stability particularly for more active prosthetic device users. The second ring seal 28 may be oriented parallel to the first ring seal 22. The second ring seal 28 is positioned farther from the opening 18 than the first ring seal 22. As shown in FIG. 2A, the second ring 28 surrounds the apertures 26.

Figure 3:
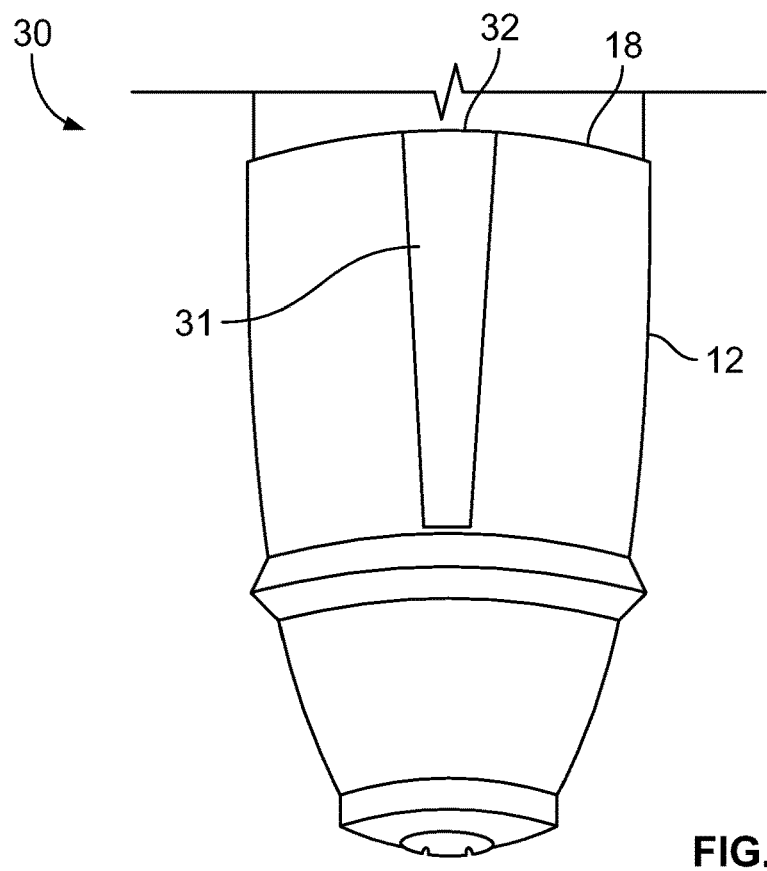
FIG. 3 is a side view of an example embodiment of a liner according to the invention.
Figure 3A:
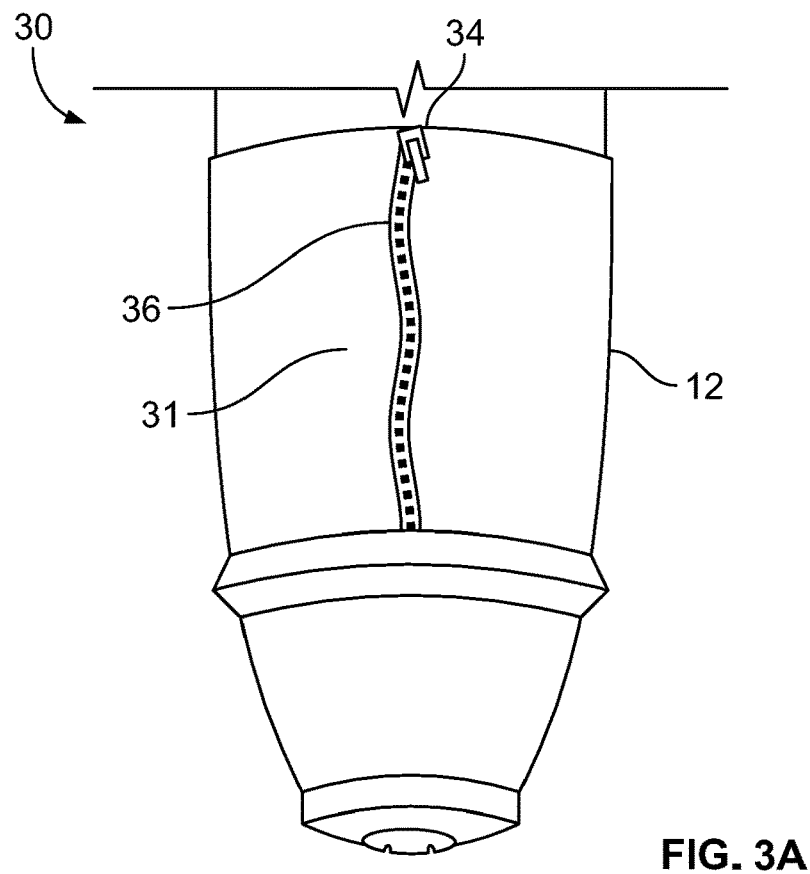
FIG. 3A is a side view of an example embodiment of a liner according to the invention showing a closure.

FIG. 3 shows an example embodiment of liner 30 comprising a seam 31 defining a split 32 in the pouch 12. The split 32 in this example facilitates easier donning of liner 30. The split 32 extends from the opening 18. In a particular embodiment, shown in FIG. 3A, liner 30 comprises a closure 34 positioned along the seam 31. Closure 34 may comprise a zipper 36.

Figure 4:
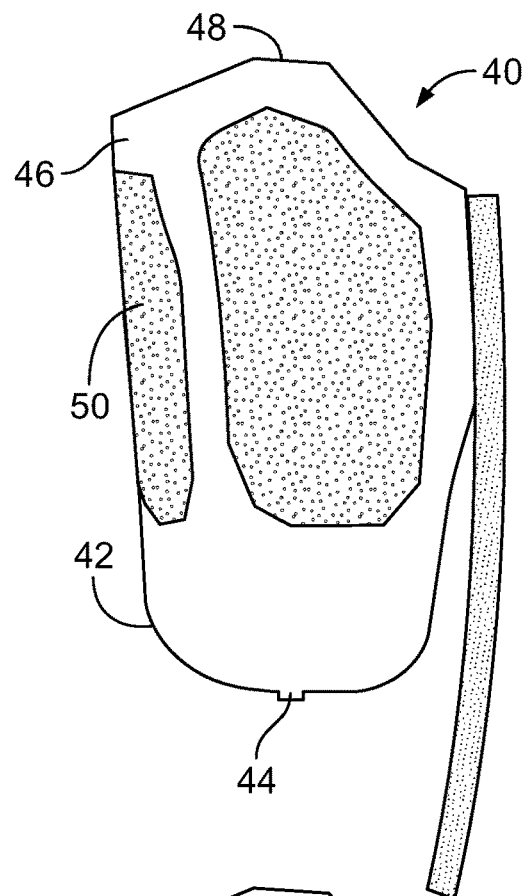
FIG. 4 is a side view of an example embodiment of an adapter, according to the invention.
Figure 4A:
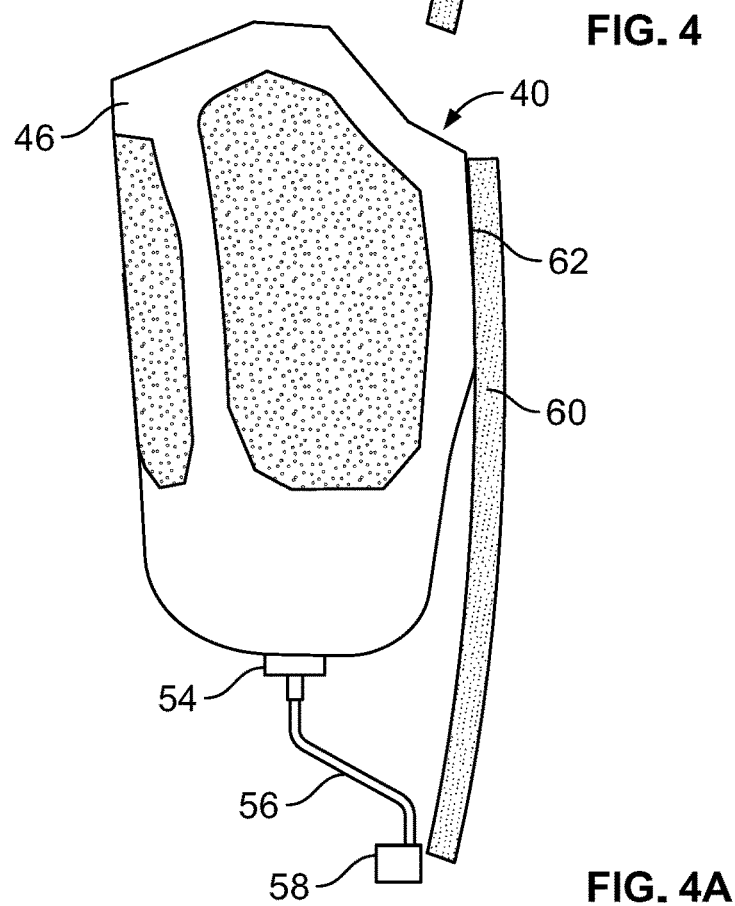
FIG. 4A is a side view of an example embodiment of an adapter, having a valve according to the invention.

FIG. 4 shows an example embodiment of an adapter 40. The adapter 40 may be fabricated from a laminated carbon fiber composite material. The adapter 40 comprises a socket 42 for receiving the residual limb. At least one hole 44 is positioned within the socket 42 for drainage therefrom. A sleeve 46 extends from the socket 42 and surrounds a central space 48. At least one vent 50 is positioned in the sleeve 46. The vent 50 may consist of an area of vent holes. As shown in FIG. 4A, the adapter 40 may also comprise a valve 54 connected to the hole 44. The valve 54 allows air to evacuate the socket during donning. The valve 54 may include a suction hose 56 connected to a pump 58 to facilitate an elevated vacuum suspension and drainage. The adapter 40 also comprises an interface 60 connecting the adapter to the prosthetic limb. The interface 60 may be attached to the adapter 40 by fasteners or bonding. The interface 60 may attach to a posterior surface 62 of the sleeve 46, as shown in FIG. 4A.

Figure 5:
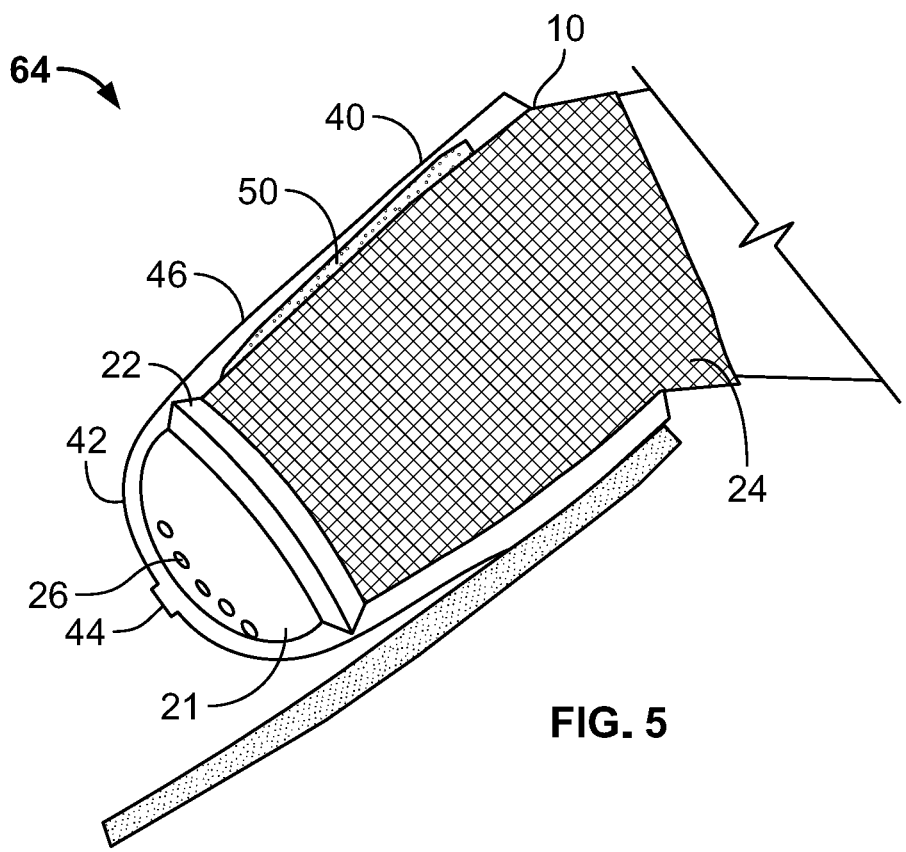
FIG. 5 is a sectional side view of an example embodiment of a liner according to the invention.
Figure 5A:
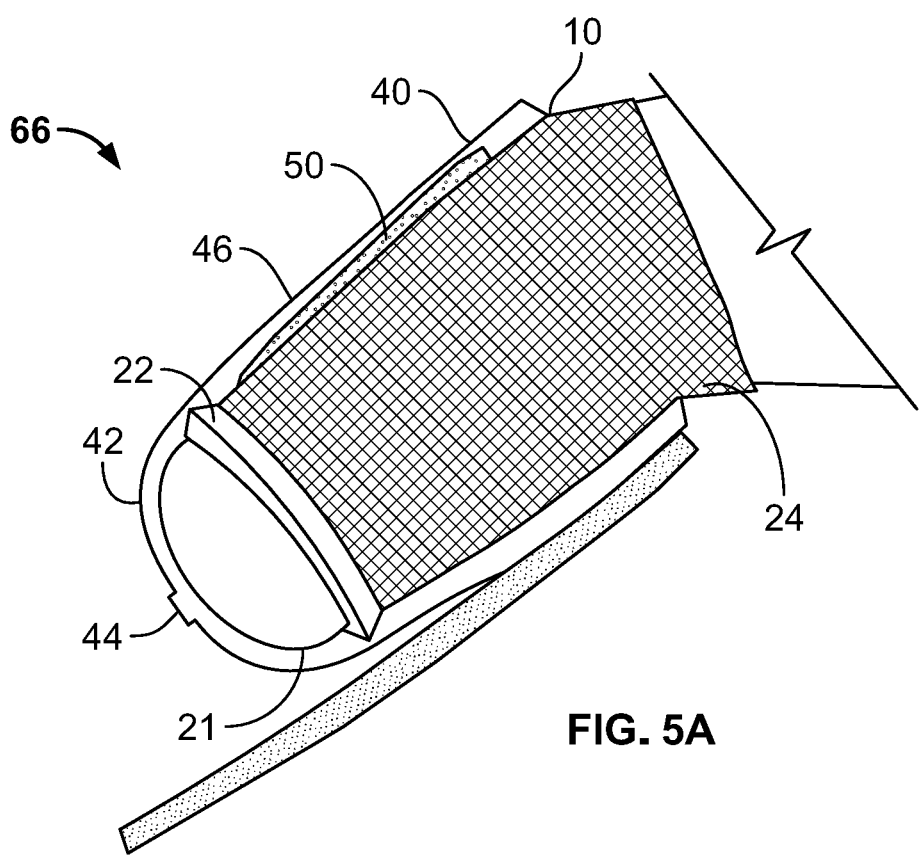
FIG. 5A is a sectional side view of an example embodiment of a liner according to the invention.

In use, the prosthetic user dons the liner 10, shown in FIG. 1, by inserting the residual limb 16 through the opening 18 into pouch 12. As shown in FIG. 5, a combination 64 comprising liner 10 and adapter 40 is then formed by inserting liner 10 into the socket 42 of adapter 40 A snug fit is preferable to prevent relative motion between the liner 10 and the sleeve 46. The socket 42 engages the first ring seal 22 of liner 10. As the seal ring 22 engages socket 42 trapped air evacuates through the hole 44. With ring seal 22 engaged with socket 42, the at least one vent 50 overlies the air-permeable material 24, providing a ventilation path to allow evaporative cooling of the residual limb. The apertures 26 in cup 21 face the hole 44 in the adapter 40 providing a fluid path away from the residual limb. Alternatively, as shown in FIG. 5A, a combination 66 of liner 10 and adapter 40 may include the cup 21 of the liner 10 without the apertures 26.

Figure 6:
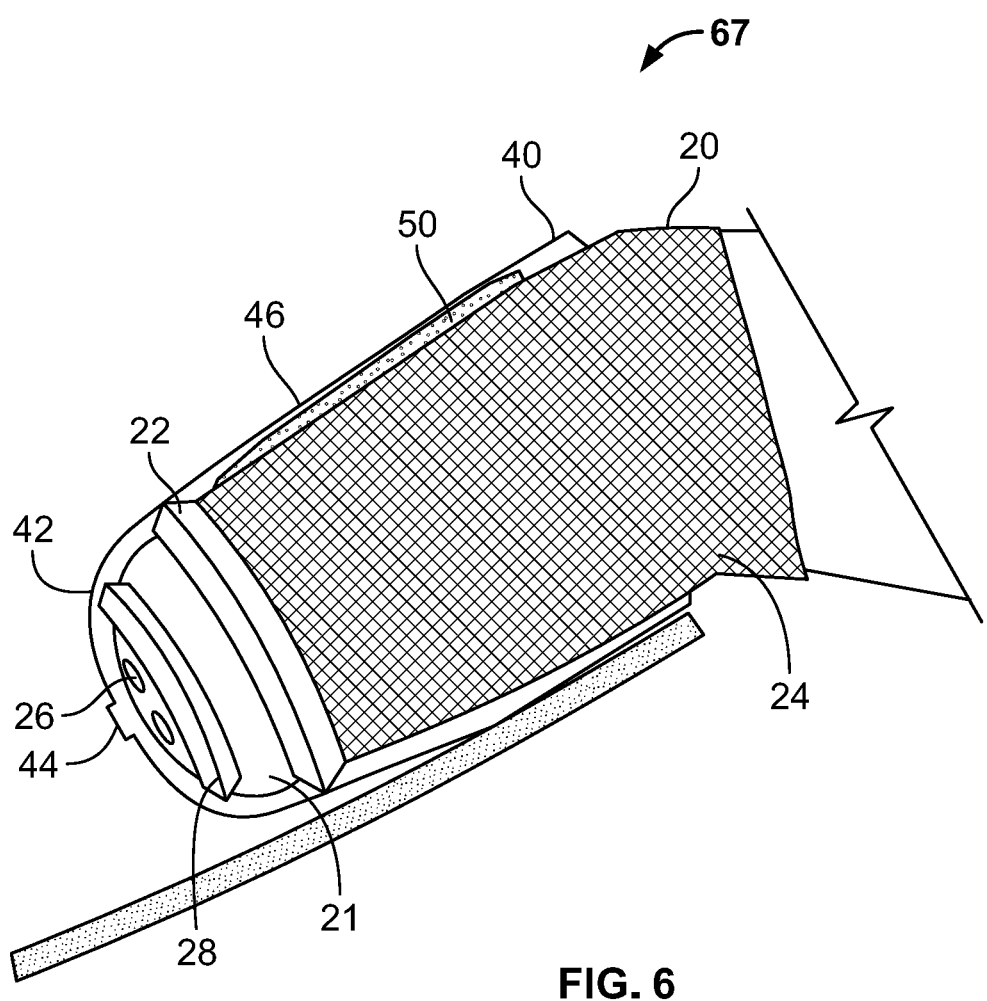
FIG. 6 is a sectional side view of an example embodiment of a liner according to the invention.

FIG. 6 shows another example embodiment of a combination 67 comprising liner 20 and adapter 40. In this example, the socket 42 engages the first and second ring seals 22 and 28 of liner 20. As the second seal ring 28 engages socket 42 trapped air evacuates though hole 44. The apertures 26 positioned in the cup 21 are surrounded by the second seal ring 28. The apertures 26 in cup 21 face the hole 44 in the adapter 40 providing a fluid path away from the residual limb. With ring seals 22 and 28 engaged with socket 42, the at least one vent 50 overlies the air-permeable material 24, to provide a ventilation path.

Figure 7:
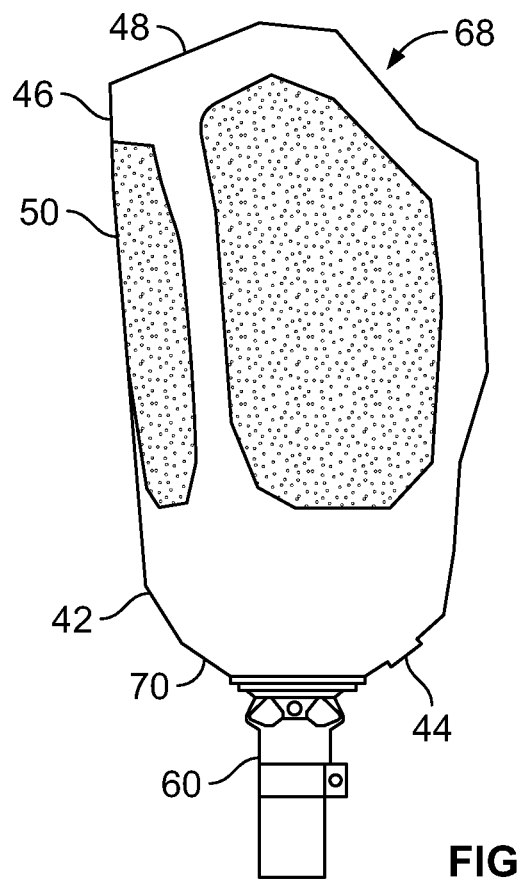
FIG. 7 is a side view of an example embodiment of an adapter according to the invention showing an interface attached to a socket.
Figure 7A:
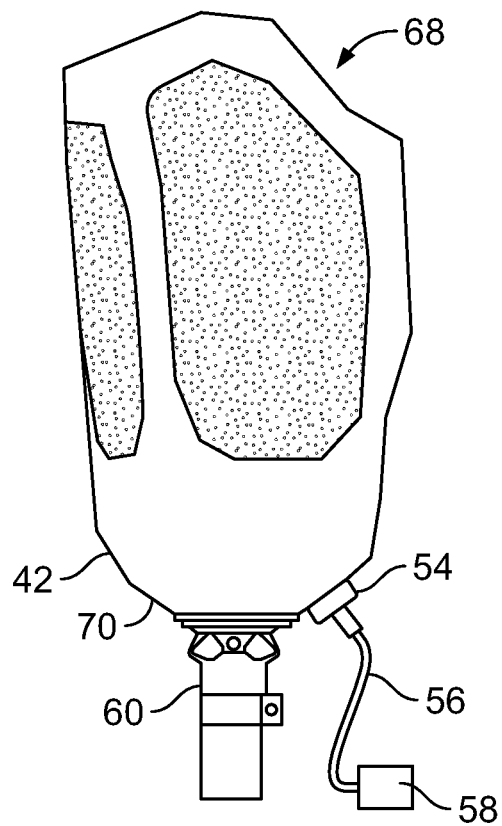
FIG. 7A is a side view of an example embodiment of an adapter according to the invention having a valve.

FIG. 7 shows an example embodiment of an adapter 68. Adapter 68 is similar to adapter 40 (see FIG. 4) except that the interface 60 connecting the adapter 68 to the prosthetic limb is attached to a distal end 70 of adapter 68. Also shown in FIG. 7, the at least one hole 44 is offset from the interface 60 sufficient to permit the attachment of valve 54, as shown in FIG. 7A. The valve 54 may include a suction hose 56 connected to a pump 58 to facilitate an elevated vacuum suspension and drainage.

Figure 8:
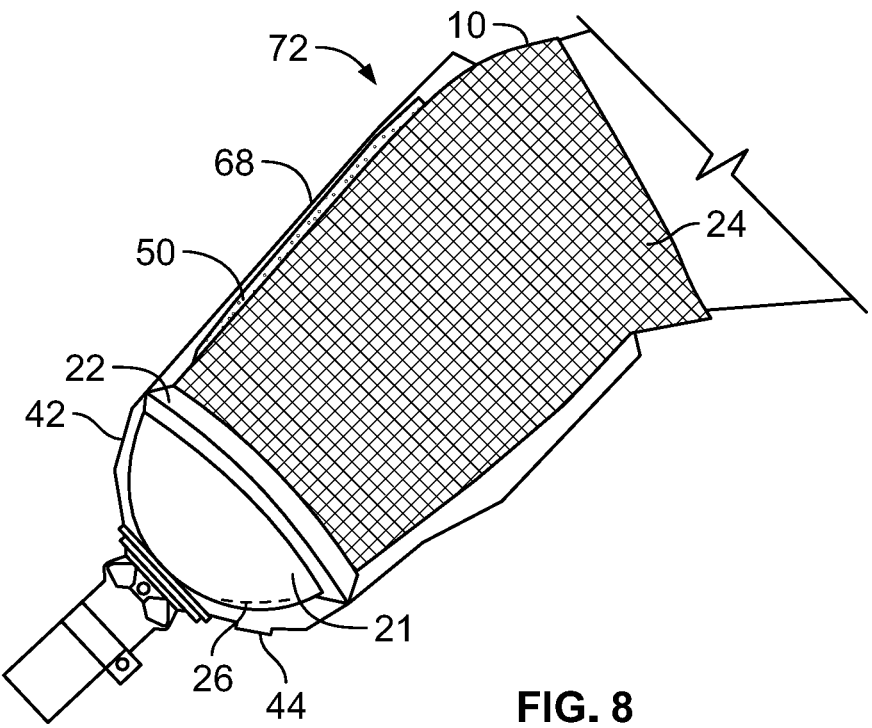
FIG. 8 is a sectional side view of an example embodiment of a liner according to the invention.
Figure 8A:
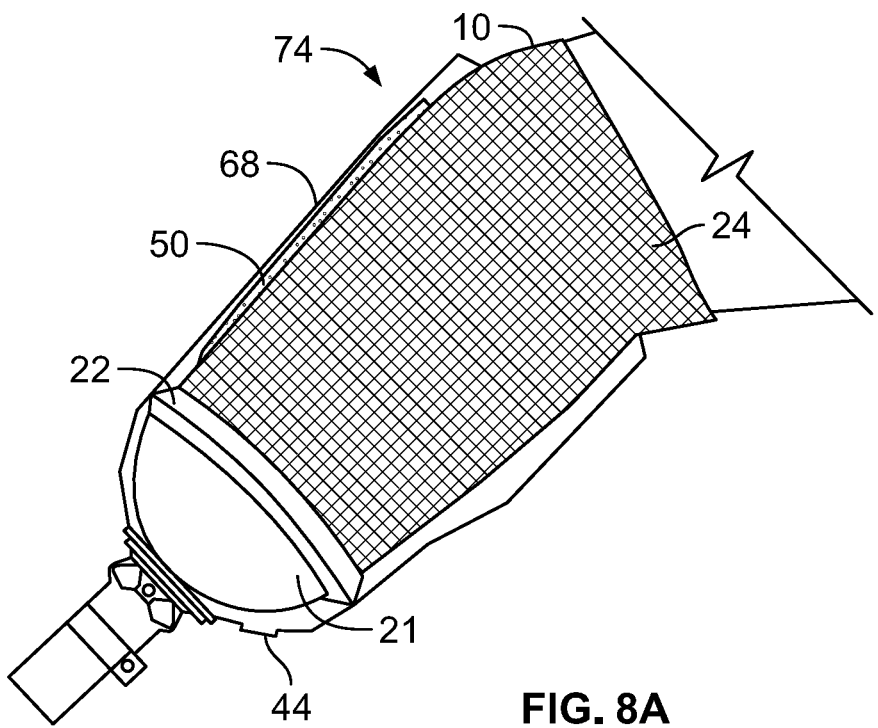
FIG. 8A is a sectional side view of an example embodiment of a liner according to the invention.

FIG. 8 shows an example embodiment of the combination 74 comprising liner 10 and adapter 68. In use, the liner 10 is inserted into the socket 42 of adapter 68. The socket 42 engages the first ring seal 22 of liner 10. As the seal ring 22 engages socket 42 trapped air evacuates through the hole 44 in adapter 68. With ring seal 22 engaged with socket 42, the at least one vent 50, shown in FIGS. 8 and 8A (see also FIG. 7), overlies the air-permeable material 24, providing a ventilation path to allow evaporative cooling of the residual limb. The apertures 26 in cup 21 of liner 10 face the hole 44 in the adapter 68 providing a fluid path away from the residual limb. Alternatively, as shown in FIG. 8A, the combination 74 comprising liner 10 and adapter 68 may include the cup 21 of the liner 10 without the apertures 26.

The liner and adapter combination as described herein is expected to remove excess moisture while maintaining suspension between the prosthetic limb and the liner.

It will be apparent to those skilled in the art that various modifications and variations can be made in the present invention without departing from the scope or spirit of the invention. Other aspects of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A liner adapted to receive a residual limb, said liner comprising:
    a pouch defining an internal volume for receiving said limb;
    an opening defined by said pouch providing access to said internal volume;
    a seam defining a split in said pouch, said split extending from said opening;
    a closure positioned along said seam, said closure comprising a zipper;
    a cup positioned on said pouch distal to said opening, said cup being air-impermeable; and
    a first ring seal attached to said pouch and surrounding said cup.

2. The liner according to claim 1, further comprising a second ring seal surrounding said cup, said second ring seal being in spaced apart relation to said first ring seal.

3. The liner according to claim 2, wherein said second ring seal is positioned farther from said opening than said first ring seal.

4. The liner according to claim 3, further comprising a plurality of apertures positioned in said cup, said apertures being surrounded by said second ring seal.

5. The liner according to claim 2, wherein said second ring seal is oriented parallel to said first ring seal.

6. The liner according to claim 1, wherein said pouch comprises an air-permeable material.

7. The liner according to claim 1, further comprising a plurality of apertures positioned in said cup.

8. In combination, a liner and an adapter, said liner adapted to receive a residual limb, said adapter for connecting said liner to a prosthetic, said liner comprising:
    a pouch defining an internal volume for receiving said limb;
    an opening defined by said pouch providing access to said internal volume;
    a cup positioned on said pouch distal to said opening, said cup being air-impermeable;
    a first ring seal attached to said pouch and surrounding said cup,
    said adapter comprising:
    a socket for receiving said cup, said socket engaging said first ring seal;
    at least one hole positioned within said socket for drainage therefrom; and
    a sleeve extending from said socket and surrounding a central space, at least one vent being positioned in said sleeve.

9. The combination according to claim 8, further comprising a second ring seal surrounding said cup, said second ring seal being in spaced apart relation to said first ring seal, said socket engaging said second ring seal.

10. The combination according to claim 9, wherein said second ring seal is oriented parallel to said first ring seal.

11. The combination according to claim 10, wherein said second ring seal is positioned farther from said opening than said first ring seal.

12. The combination according to claim 8, wherein said pouch comprises an air-permeable material.

13. The combination according to 12, wherein said at least one vent overlies said air-permeable material.

14. The combination according to claim 8, further comprising a plurality of apertures positioned in said cup, said apertures being surrounded by said second ring seal, said apertures facing said at least one hole.

15. The combination according to claim 8, further comprising an interface to said prosthetic, said interface is attached to a distal end of said adapter.

16. In combination, a liner and an adapter, said liner adapted to receive a residual limb, said adapter for connecting said liner to a prosthetic, said liner comprising:
    a pouch defining an internal volume for receiving said limb;
    an opening defined by said pouch providing access to said internal volume;
    a cup positioned on said pouch distal to said opening, said cup being air-impermeable;
    a first ring seal attached to said pouch and surrounding said CUD;
    said adapter comprising:
    a socket for receiving said cup, said socket engaging said first ring seal;
    at least one hole positioned within said socket for drainage therefrom;
    a plurality of apertures positioned in said cup, said apertures facing said at least one hole;
    a sleeve extending from said socket and surrounding a central space; and
    an interface to said prosthetic, said interface being attached to a posterior surface of said sleeve.

17. The combination according to claim 16, further comprising an interface to said prosthetic, said interface being attached to a distal end of said adapter.

18. In combination, a liner and an adapter, said liner adapted to receive a residual limb, said adapter for connecting said liner to a prosthetic, said liner comprising:
    a pouch defining an internal volume for receiving said limb;
    an opening defined by said pouch providing access to said internal volume;
    a cup positioned on said pouch distal to said opening, said cup being air-impermeable;

a first ring seal attached to said pouch and surrounding said CUD;

said adapter comprising:

a socket for receiving said cup, said socket engaging said first ring seal;

at least one hole positioned within said socket for drainage therefrom; and a sleeve extending from said socket and surrounding a central space; and an interface to said prosthetic, said interface being attached to a posterior surface of said sleeve.

\* \* \* \* \*